United States Patent
Legay et al.

(10) Patent No.: US 7,440,801 B2
(45) Date of Patent: Oct. 21, 2008

(54) IMPLANTABLE CARDIAC PACEMAKER WITH AUTOMATIC CONTROL OF THE CONNECTION OF A PROBE AND THE IMPLANTATION OF THE CASE

(75) Inventors: Thierry Legay, Las Briis (FR);
Dominique Decoene, Pontchartrain (FR)

(73) Assignee: Ela Medical S.A.S., Montrouge (FR)

( * ) Notice: Subject to any disclaimer, the term of this patent is extended or adjusted under 35 U.S.C. 154(b) by 358 days.

(21) Appl. No.: 11/186,623

(22) Filed: Jul. 20, 2005

(65) Prior Publication Data
US 2006/0052833 A1    Mar. 9, 2006

(30) Foreign Application Priority Data
Jul. 23, 2004    (FR)    ................... 04 08162

(51) Int. Cl.
*A61N 1/00*    (2006.01)
(52) U.S. Cl. ........................................................ 607/9
(58) Field of Classification Search ...................... 607/9, 607/27, 28
See application file for complete search history.

(56) References Cited
U.S. PATENT DOCUMENTS

| | | | |
|---|---|---|---|
| 5,370,666 A | 12/1994 | Lindberg et al. | |
| 5,522,856 A | 6/1996 | Reinman | |
| 5,534,018 A | 7/1996 | Wahlstrand et al. | |
| 5,713,932 A * | 2/1998 | Gillberg et al. | ................ 607/27 |
| 6,016,447 A | 1/2000 | Juran et al. | |
| 6,317,633 B1 * | 11/2001 | Jorgenson et al. | .............. 607/28 |

FOREIGN PATENT DOCUMENTS

EP    1 438 985 A1    7/2004

* cited by examiner

*Primary Examiner*—George Manuel
(74) *Attorney, Agent, or Firm*—Orrick Herrington & Sutcliffe, LLP

(57) ABSTRACT

An implantable cardiac pacemaker with automatic control of the connection of a probe and the implantation of the case. The device includes a generator and its energy source. The generator includes: circuits for scanning battery consumption, able to measure current output by the battery and to deliver a measured value of the output current; comparator circuits, able to compare the current value measured with a pre-programmed value of threshold of current. It includes moreover circuits suited to: detect and count the spontaneous depolarizations collected between the aforementioned terminals of the head of connector; to compare the number of depolarizations thus counted with a pre-programmed threshold of counting; and to deliver a signal of suspicion of implantation in the event of crossing of this threshold of counting.

20 Claims, 4 Drawing Sheets

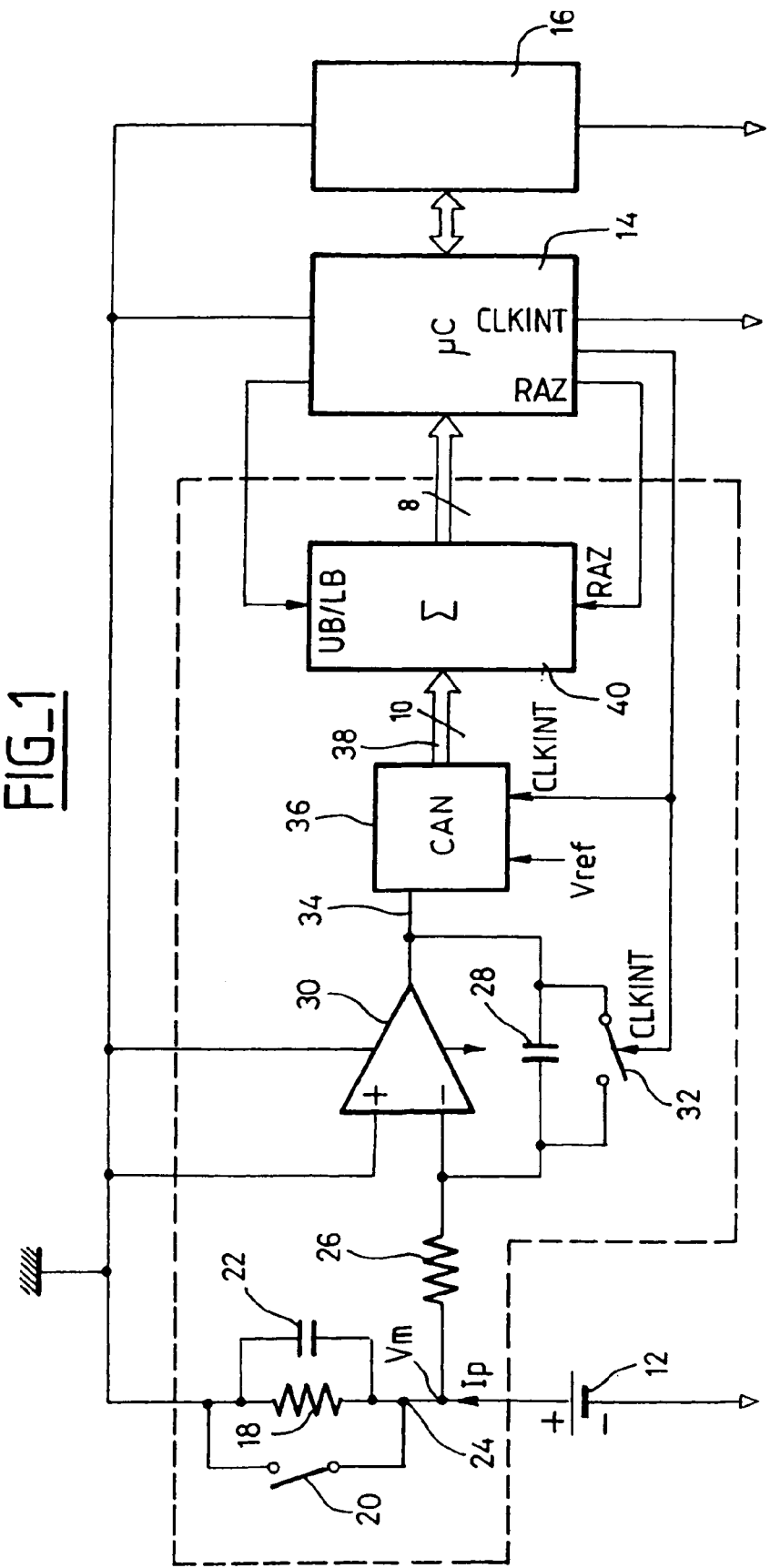
FIG_1

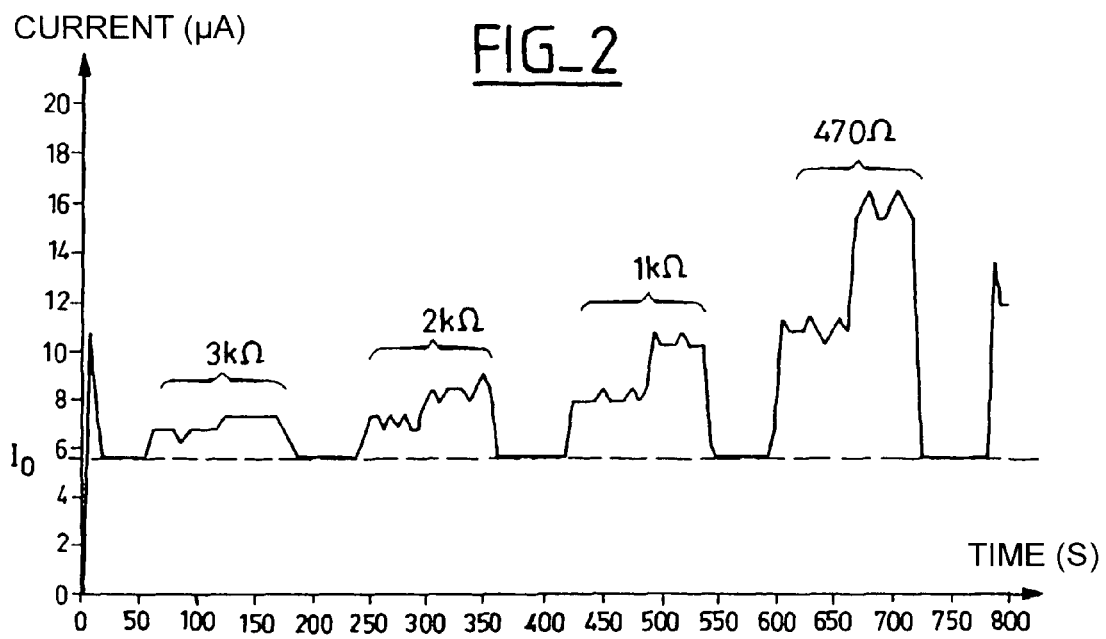
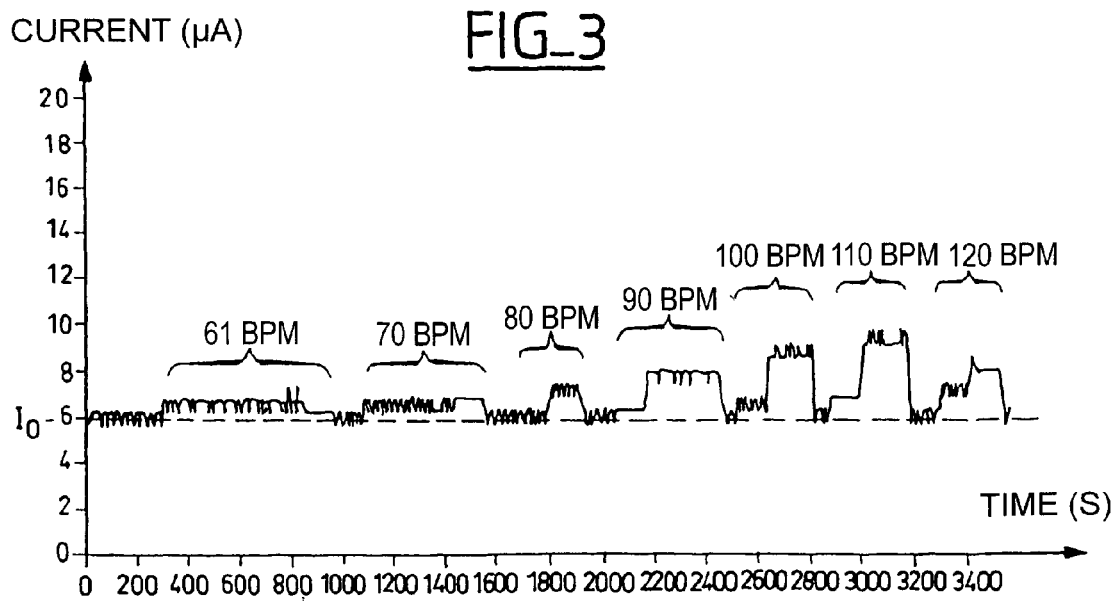

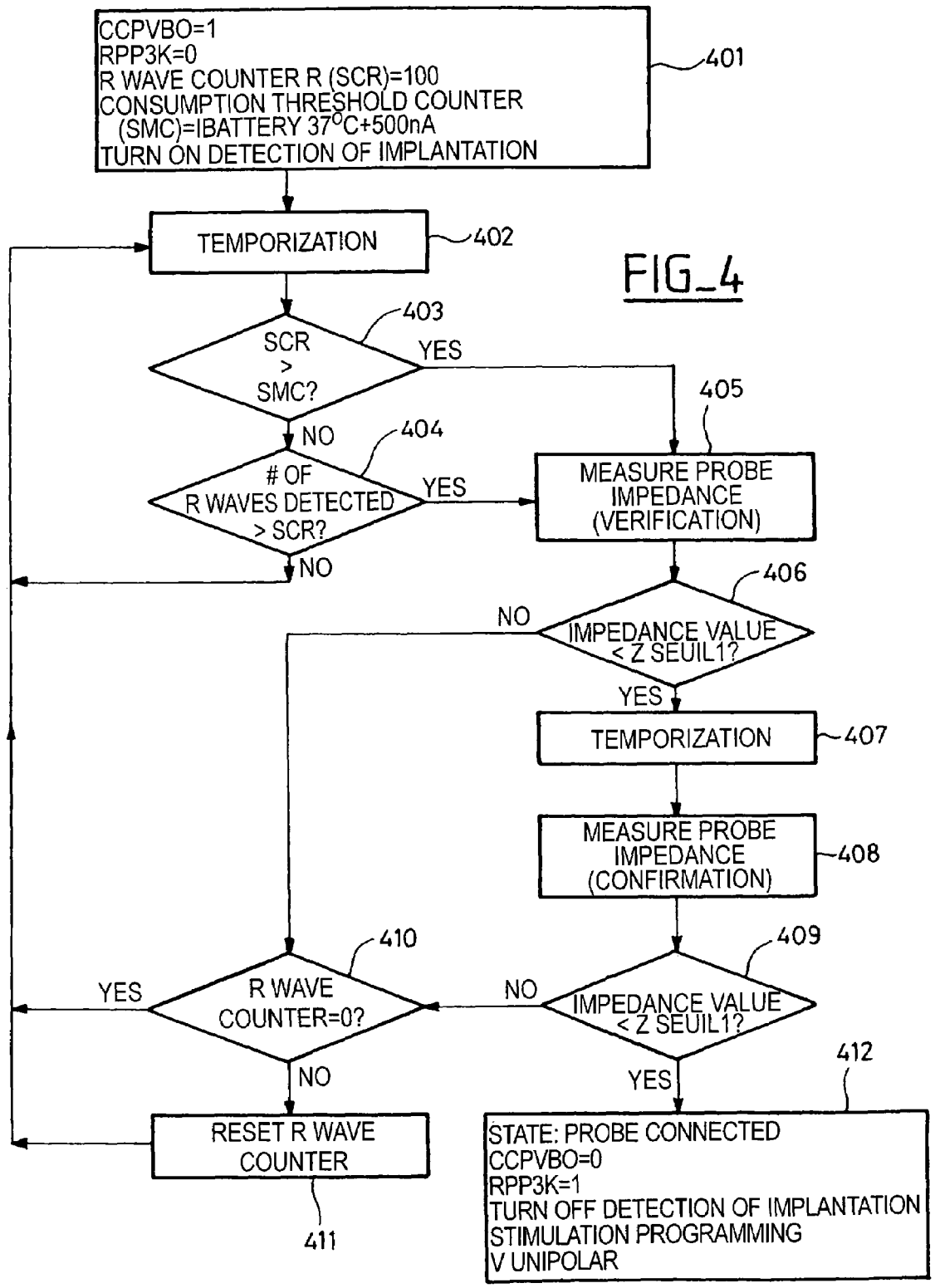

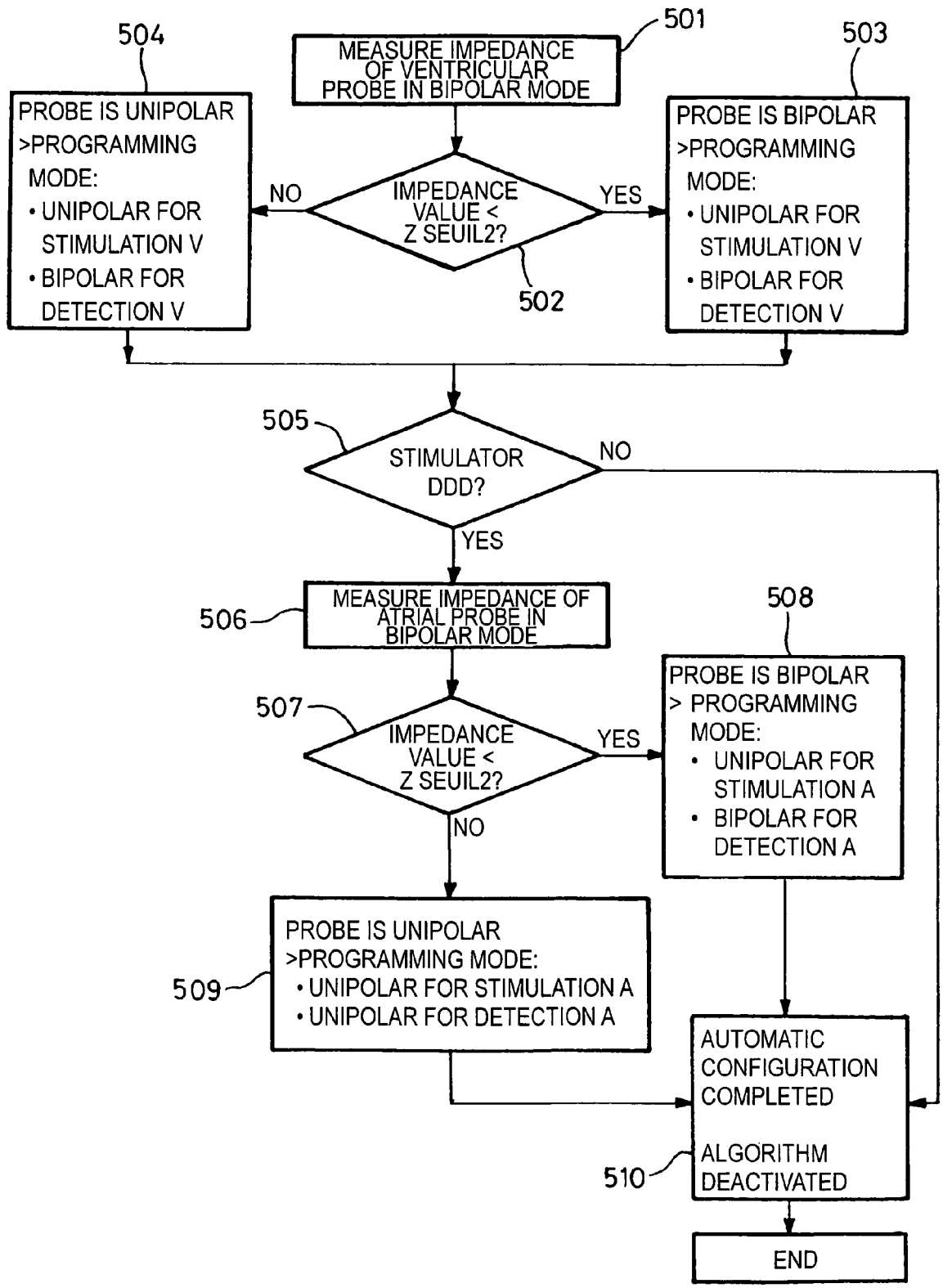

IMPLANTABLE CARDIAC PACEMAKER WITH AUTOMATIC CONTROL OF THE CONNECTION OF A PROBE AND THE IMPLANTATION OF THE CASE

FIELD OF THE INVENTION

The present invention relates to "active implantable medical devices" as defined by the Jun. 20, 1990 directive 90/385/CEE of the Council of the European Communities, and more particularly to cardiac pacemakers, "multisite devices" (triple or quadruple chamber), defibrillators, and/or cardiovertors that are able to deliver to the heart pulses of low energy for treatment of cardiac rhythm problems.

BACKGROUND OF THE INVENTION

The above-identified devices comprise a generator containing in the same case various electronic circuits and an energy source. When such devices are implanted, the generator is mechanically and electrically connected to a probe equipped with electrodes for intracardiac stimulation, making it possible to detect depolarization potentials of the myocardium and to deliver stimulation impulses produced by the generator.

The probe connection must be capable of being detected automatically by the generator, so as to activate various functionalities, e.g., launch algorithms, initialize a certain number of parameters, and memorize starting data. U.S. Pat. Nos. 5,522,856 and 5,370,666 disclose an insertion of the probe by uninterrupted screening of terminals of a connector head of the device and measurement of the impedance between these terminals. In the absence of a probe, this impedance is extremely high, but upon insertion of a probe the value decreases below a certain threshold whose crossing, when detected, causes the pacemaker to change from a sleeping mode to a completely functional mode. Continuous screening of the impedance, however, impacts energy consumption and lifespan of the battery, because it requires with each measurement injection of a current between terminals of the probe and activation of circuits for measuring the corresponding collected voltage. Another possibility consists of using an external programmer to activate the generator at the end of an implantation. This technique, however, requires intervention of a surgeon.

One of the goals of the present invention is to propose a circuit that can automatically detect connection of a probe, without requiring direct and permanent measurement of the impedance between terminals, and without recourse to an external programmer.

In addition, it is generally possible to connect to the same generator two different types of probes, monopolar or bipolar, at the choice of the surgeon and according to the type of pathology to be treated. In the case of a monopolar (or "unipolar") probe, detection and stimulation are operated between the single electrode and the metal case of the generator, while in a bipolar probe, detection and stimulation can be carried out either in a differential mode between two electrodes of the probe, or in a common mode between the case of the generator and one or the other of the probe electrodes. Of course, many internal parameters of the generator must be selected according to the type of probe used, monopolar or bipolar, e.g., commutation of the terminals having to be used, collection of depolarization signals, adjustment of stimulation parameters, and modification of the algorithms controlling the microprocessor. Any error in selecting the type of operating mode (monopolar or bipolar) can involve serious consequences. For example, if the device is programmed for a bipolar stimulation, but is equipped with a monopolar probe, this error can cause a loss of capture and application of an inappropriate stimulation, with a risk for the patient.

Another goal of the present invention is to propose a device that can, in addition to automatically detecting connection of a probe, determine the type of probe being used, i.e., monopolar or bipolar, and upon doing so, commutate and parameterize appropriate circuits and algorithms of the device. This function, managed automatically by the device, makes it possible to minimize, if not avoid, any risk of error resulting from non-conformance between type of probe used and operating mode of the device. One thus avoids, for example, any risk of bipolar stimulation applied erroneously to a monopolar probe.

Automatic determination of the type of polarity also makes it possible to take into account the fact that in the majority of countries the pacemaker is delivered in unipolar configuration, to ensure a stimulation in any event. But today in many cases it is a bipolar probe that is implanted, which requires parameterization of the generator only after the probe is connected. The system according to the present invention, by automatically determining the polarity to be used upon implantation of the device, authorizes an automatic setting of the parameters of the generator without requiring intervention of the surgeon.

Another goal of the invention is to propose a device making it possible to take into account the particular configuration where the probe was implanted and connected to the case of the pacemaker, but where this case is not yet introduced into the implantation site (i.e, the incision or pocket in the patient into which the surgeon plans to place the impulse generator). The case is thus not yet in contact with tissues of the patient and cannot be used as a reference potential. In such a situation it is preferable to avoid a monopolar stimulation of the probe, because the delivered impulses would be ineffective due to absence of a ground. However, during this intermediate phase, it is desirable to deliver a bipolar stimulation if a ventricular bipolar probe is implanted and already connected.

The device of the present invention makes it possible to take into account this intermediate configuration, until implantation of the device. It is only after detection of the implantation that the corresponding functions of the pacemaker will be activated, and the polarity configured, i.e., monopolar or bipolar. Due to the automatic activation of the pacemaker functionalities, the surgeon will never need to force a particular mode of stimulation before implantation of the generator in the pocket, or after completion of implantation. It will be sufficient for the surgeon to connect the probe, whatever its type, with the generator, and safety will be automatically ensured during and after the intervention.

OBJECTS AND SUMMARY OF THE INVENTION

To achieve the above-mentioned goals, the present invention proposes a device of a known general type, for example, according to the above-mentioned U.S. Pat. Nos. 5,522,856 and 5,370,666, i.e., including a case and, in the case, a generator and a power supply battery for the generator, the generator being able to produce stimulation impulses in monopolar mode or bipolar mode, and being connected to a connector head equipped with at least two terminals able to be connected to electrodes of a monopolar or bipolar detection and stimulation probe connected to the connector, this probe capable of being a monopolar probe or a bipolar probe; and including means for detecting the presence of a probe connected to the connector.

In one embodiment of the invention, the aforementioned detection means include, in combination: means for scanning consumption by the generator of output current from the battery, capable of measuring the current output by the battery and delivering a measured value of the current; comparator means, able to compare the measured current value with a pre-programmed current threshold value such that crossing of the threshold determines the presence of a probe connected to the connector. The detection means also includes means capable of (i) detecting and counting the spontaneous depolarizations collected between the aforementioned terminals of the connector head; (ii) comparing the number of depolarizations thus counted with a pre-programmed counting threshold; and (iii) delivering a signal of suspicion of implantation in the event of crossing of this counting threshold.

Advantageously, the measuring means includes:
(i) integrator means, capable of delivering at regular intervals a succession of measured values representative of the value, integrated throughout a predetermined integration period, of the output current delivered by the battery; and/or
(ii) analog/digital converters means, capable of delivering the measured value in the form of a digital word; and/or
(iii) summing means, capable of delivering the measured value in the form of a cumulative sum calculated throughout a predetermined summation period.

The device can also include impedance test means, conditionally activated in the event of a crossing of the current threshold by the measured value, able to measure the probe impedance between the aforementioned terminals of the connector head, to compare the impedance value thus measured with a pre-programmed impedance threshold, and to deliver a signal of suspicion of implantation in the event the measured impedance is lower than this impedance threshold.

Preferably, the scanning means comprise controlling means, which are triggered in response to delivery of the signal of suspicion of implantation, and are capable of: initiating a temporization (i.e., a delay interval), and at the end of temporization, reiterating the test function, and in the event of test delivering again a signal of suspicion, delivering a signal of confirmation of implantation.

In this last case, the scanning means advantageously comprise means, triggered in response to delivery of a signal of confirmation of implantation, capable of operating the generator in a mode of monopolar and bipolar stimulation simultaneously, to a mode of monopolar stimulation. Advantageously, the scanning means will comprise means, triggered in response to the delivery of a signal of confirmation of implantation, capable of detecting the type of probe, monopolar or bipolar, whose electrodes are connected to at least two terminals. This detection means can include means for measuring probe impedance between the terminals of the connector head, and means capable of comparing the value of the impedance thus measured with a pre-programmed threshold of discrimination of probe.

Lastly, the device can also comprise means capable of configuring, in response to the type of probe detected, the operating mode, monopolar or bipolar, of the stimulation circuits and detection of the generator associated with the aforementioned probe.

BRIEF DESCRIPTION OF THE DRAWING

Further benefits, features, and characteristics of the present invention will become apparent to a person of ordinary skill in the art in view of the following detailed description of preferred embodiments of the present invention, made with reference to the annexed drawings, in which:

FIG. 1 is a schematic view of a circuit for measuring consumption by the generator of output current from the battery incorporated in the device according to the invention;

FIG. 2 is an example of measured current consumption, variable according to various values of impedance of the stimulation probes;

FIG. 3 is an example of measured current consumption, variable according to the frequency of the detected depolarization waves;

FIG. 4 is a flow chart of the various stages allowing detection of implantation of the device; and FIG. 5 is a flow chart of the various stages making it possible to ensure configuration of polarity of the stimulation and detection circuits.

DETAILED DESCRIPTION OF THE INVENTION

With regard to its software aspects, the present invention can be implemented by suitable programming of the control software of a known pacemaker, for example, implantable medical devices marketed by ELA Médical, Montrouge, France, such as the Symphony and Rhapsody branded devices. These are programmable devices with memory and microprocessors and circuits for receiving, formatting, and processing electric signals collected by probes bearing cardiac electrodes, and delivering stimulation impulses to these electrodes. It is possible to download to memory the software that will be carried out to implement the functions of the invention described below. Adaptation of these apparatuses and the creation of software suitable to implement the functionality described herein are deemed within the capability of the person of ordinary skill in the art, and will not be described in detail herein.

The following description relates primarily to implementation of the ventricular stimulation function. Indeed, even in the case of a "double chamber" apparatus, a purpose of the implantation detection is to make certain that ventricular stimulation is possible and effective. If only atrial stimulation were possible and effective, implantation of the device would not automatically be regarded as not implanted, because the contribution of the atrium in a "double chamber" device is less important. However, everything described herein within the context of ventricular stimulation applies equally to atrial stimulation. In the same way, in the case of a multisite device, the same sequence of stages is similarly applicable to each stimulation output.

The principle of the invention rests on permanent analysis or screening of consumption by the generator of output current from the battery of the device. This screening is permanent, including during shipment of the device. It is thus possible at any moment to announce a change of behavior of the prosthesis, revealed by an increase in current consumption. In particular, the prosthesis implantation will cause an increase in current consumption because of stimulation on a load which is no longer infinite (as it was the case in the packaging), because of the detection of cardiac signals activating the digital filters, whose consumption depends on the input signal, as well as the waking up of the microcontroller carrying out the specific software instructions on each new endocardial detection.

The screening of this current consumption is operated by a hardware circuit 10 whose circuit diagram is given in FIG. 1. In practice, the current consumption of the circuit 10 is very low, e.g., about 0.2 µA, which is a value acceptable even for a permanent operation. The circuit 10 is connected to a battery 12, of which it will measure the current Ip, and, to a microcontroller 14, which is of a conventional type, making it possible to run the software of the device and comprising, e.g., read-only memories and random-access memories, timers, DMA controllers, a system of interruption, and a clock. This microcontroller 14 is interfaced with a circuit 16 containing the dedicated electronics of the device, with its circuit stages of stimulation, detection amplifiers, data processing sequences for signals delivered by the sensors, telemetry system, voltage, current, and time references.

A battery 12 supplies all of the electronic circuits of the device and also provides energy for the stimulation impulses. The current Ip provided by the battery 12 crosses a measuring resistor 18 when screening of the current is activated, i.e., when switch 20 is open (if it is no longer necessary to carry out this screening, for example, after implantation of the device, switch 20 will be closed and the hardware circuit 10 de-activated). A capacitor 22, in parallel with resistor 18, is used to filter fast current transients crossing this resistance.

The current Ip passing through resistor 18 produces a voltage $V_m$ proportional to the current in 24. This voltage is integrated by a circuit made up of resistor 26, capacitor 28, and operational amplifier 30. The time-constant of integration is selected to be relatively short, typically 50 ms, in order to avoid saturation of amplifier 30. The integration cycle is defined by signal CLKINT produced by microcontroller 14, which controls switch 32. During the integration phase, switch 32 is opened and, at the end of integration, the voltage integrated, present in 34 at output of amplifier 30, is converted into a digital value by an analog/digital converter 36. Switch 32 is then closed to discharge capacitor 28 before the beginning of a new integration cycle at 50 ms. The elementary values of integration over 50 ms, delivered via bus 38 upon exiting converter 36, are summed by adder 40, during a time fixed by the signal RESET produced by microcontroller 14. This duration of summation is selected to be sufficiently long, typically about 6 s, to be able to integrate several cardiac cycles of the device.

At the end of the approximately 6 s time of integration, the result of the adder, on two bytes, is read twice by the microcontroller 14 (by the signal of selection UB/LB of selection of the first byte then of the second byte). When the microcontroller 14 has acquired an average value of battery current $I_p$ over 6 s, it resets adder 40 by signal RESET in order to start a new cycle of integration of the battery current.

Measuring current consumption over 6 s gives a suitable representation at the same time of the total current consumption of the circuits of the device and current consumption related to stimulation. The resolution of measurement is selected sufficiently low to make it possible to discriminate the starting or stopping of the principal function blocks of the prosthesis, like discriminating changes in the stimulation parameters. This resolution must be lower than 1 µA, and is advantageously selected to be about 0.16 µA. This resolution makes it possible to detect connection of a probe in the case of the generator.

FIG. 2 shows the variation of current for various probe impedance values in the absence of detected cardiac signals. When no probe is connected, the current has reference value $I_0$. When a probe is connected, one can observe two stages of consumption, corresponding respectively to connection of the ventricular probe, followed by connection of the atrial probe. FIG. 2 shows current fluctuations in the case of a connection of a probe of high impedance (3 kΩ), then disconnection of this probe and connection of a probe of a slightly lower impedance (2 kΩ). The current consumed is higher when probe impedance is low and one can see that variation of the current is detectable even for probes of high impedance (3 kΩ), and even if only the ventricular probe is connected (first stage of the variation).

FIG. 3 shows variations of the current consumed according to the frequency of the cardiac signals detected by the device, for various increasing rate frequencies: 61 bpm, 70 bpm, 80 bpm . . . 120 bpm. Compared to the reference current value $I_0$ in the absence of a probe, one notes that, for the lowest frequencies, the activity of the amplifiers and digital filters processing the cardiac signals, as well as the waking up of the microcontroller carrying out the algorithms, induce a consumption that is at the limit of what the device can detect. To mitigate this disadvantage, and to compensate for the fact that the consumption can remain low in the event of inhibited stimulation (because of the presence of a patient's own rhythm), the invention also envisages counting spontaneous ventricular depolarizations (R-waves). This system of counting R-waves, which provides additional security, will be further described in reference to FIG. 4. The counting of R-waves remains optional, however, if measurement of the battery current offers a high enough resolution.

FIGS. 4 and 5 are flow charts detailing the successive stages of implementation of the invention, first to detect implantation (FIG. 4), and then to configure in a suitable way the stimulation/detection polarity of the device (FIG. 5). Initially, preferably at the end of the manufacturing cycle of the apparatus, when the apparatus is in a sterile package, a certain number of parameters are initialized. The ventricular terminal proximal ("RING") and the ground of the case ("CASE") are shorted-circuit by a control CCPVBO set to 1. By short-circuiting these electrodes, the implant is configured to simultaneously deliver a stimulation in bipolar mode and monopolar mode. Thus, whether or not the case is in contact with tissues of the patient, the ventricular stimulation will be effective since a ventricular probe will have been implanted and connected to the prosthesis.

In addition, an indicator RPP3K is set to 0 to indicate that the apparatus has not been implanted, and programmable thresholds are defined—counting of the R-waves (typically 100), and consumption threshold SMC, corresponding to a suspicion of implantation. The consumption threshold SMC is preferably initialized with the value of the current consumed by the prosthesis at 37° C. on infinite load (i.e., an open circuit), increased by a significant, programmable value revealing a possible implantation (typically 500 nA). The cycle of implantation detection is then launched ("ON").

After these initialization stages 401, the device carries out a temporization having a duration that is greater than or equal to the duration of a measurement of the battery current, e.g., a temporization of 6.25 s (stage 402).

At stage 403, the measured current consumption value is compared with the current consumption threshold SMC:

(i) if the threshold is exceeded, then a measurement of probe impedance is taken by way of verification, in monopolar mode for the ventricle (stage 405);

(ii) if the threshold is not exceeded, a test is operated at stage 404 to monitor occurrence of R-waves; if the number of detections exceeds a threshold SCR, leaving suspect an implantation because of collection of these waves, then stage 405 of checking is carried out. In the contrary case, a new iteration is triggered (return to temporization 402 to await a new measurement of the consumed current).

The impedance value measured at stage 405 is compared with a discriminatory (threshold) value $Z_{seuil1}$, for example 2 kΩ, corresponding to the value of the highest impedance capable of being met (stage 406):

(i) if the $Z_{seuil1}$ threshold is crossed, an implantation is suspected, which will have to be confirmed by stages 407, 408, 409, and 412;

(ii) if the $Z_{seuil1}$ threshold is not crossed, the counter of R-waves is eventually reset to zero after checking its value (stages 410, 411) and a new iteration is committed (return at stage 402);

If the checking carried out at stages 405 and 406 appears positive, it is advisable to carry out a checking before deciding if the prosthesis is really connected to these probes and implanted. This confirmation must, however, be carried out after a temporization (stage 407), allowing the expert who would have connected the probe and placed the case in the implantation pocket to re-operate quickly to refine the implantation conditions (e.g., position of the probes, case, or bindings).

After temporization 407, a measurement of probe impedance is taken (stage 408) to confirm that the case and a ventricular monopolar probe are well in place and correctly connected. The discrimination criterion (stage 409) is identical to the aforementioned criterion (stage 406). If implantation and connection of the probe are confirmed, then (stage 412):

(i) the short-circuit between the ventricular proximal electrode and the ground of the case is removed (CCPVPO='0') and the implantation indicator is positioned (RPP3K='1');

(ii) the implantation detection algorithm is deactivated ("OFF"), involving the closing of switch 20 (FIG. 1); and (iii) the ventricular stimulation is programmed in monopolar mode.

The following phase, illustrated in FIG. 5, consists of seeking the polarity of the present probes to choose, preferentially, a configuration of bipolar detection if a bipolar probe is connected, and a monopolar stimulation configuration by default. The search for polarity starts with the ventricular probe (stages 501 to 504), and then, if the apparatus is a double chamber apparatus (stage 505), with the search for polarity of the atrial probe (stages 506 to 510).

Stage 501 is a measurement of impedance of the ventricular probe in bipolar mode, i.e., between the proximal electrode ("RING") and the distal electrode ("TIP"). The result is compared (stage 502) to a threshold $Z_{seuil2}$, preferably selected to be lower or equal to $Z_{seuil1}$ (a $Z_{seuil2}$ value of 2.5 kΩ makes it possible, for example, to take into account the fact that the bipolar impedance can be higher than the monopolar impedance). If the measured value is lower than $Z_{seuil2}$, then one is in the presence of a bipolar probe (stage 503) and ventricular detection is configured to be in bipolar mode. Preferably, one chooses to maintain the ventricular stimulation in monopolar mode, which constitutes maximum safety for the patient and the doctor (who, later on, can always reprogram the device to operate in a bipolar mode). In the contrary case, the probe is a monopolar probe (stage 504) and stimulation and detection are programmed to operate in a monopolar mode.

Stage 505 tests if the apparatus model is of the double chamber type, because if so, it is necessary also to configure the atrial stage (stages 506 to 509, homologous with stages 501 to 504). At stage 510, the automatic configuration of the device is completed, and the algorithm is de-activated. For a multisite system, this stage 510 would be replaced by the screening of another stage following the same principle, i.e., checking to determine which type of probe is connected and then configuring it automatically.

One skilled in the art will appreciate that the present invention can be practiced by other than the described embodiments which are presented for purposes of illustration and not of limitation.

We claim:

1. An active implantable medical device comprising:
a case, said case comprising a generator and a power supply battery for the generator, said battery having an output current, and said generator capable of producing monopolar stimulation impulses and bipolar stimulation impulses from said output current;
a connector head connected to said case and equipped with at least two terminals capable of being connected to electrodes of a detection and stimulation probe, said probe capable of being a monopolar probe or a bipolar probe; and
means for detecting the initial connection of a probe to the connector, said means comprising:
means for scanning a consumption by the generator of the battery output current, said scanning means being capable of measuring the output current over a first time interval and delivering a measured value of the current;
comparator means capable of comparing the measured value of the current with a pre-programmed threshold current value and indicating that the probe is connected to the connector in response to the measured value exceeding the pre-programmed threshold; and
means responsive to the measured value not exceeding the pre-programmed threshold current value for:
detecting and counting spontaneous depolarizations collected between the terminals of the connector head;
comparing the number of depolarizations thus counted with a pre-programmed counting threshold; and
delivering a signal of potential initial connection in the event the number of depolarizations thus counted crosses the counting threshold to change a functional mode of the device.

2. The device of claim 1, wherein the battery consumption scanning means comprise integrator means capable of delivering with regular intervals a succession of measured values representative of the value of the battery output current, integrated throughout a predetermined integration period.

3. The device of claim 1, wherein the battery consumption scanning means comprise analog/digital converters means capable of delivering a digital word corresponding to the measured value of the current.

4. The device of claim 3, wherein the measuring means comprises summing means capable of delivering the measured value of the current in the form of a cumulative sum operated throughout a predetermined summation period.

5. The device of claim 1, further comprising impedance test means, conditionally activated in the event the measured value of the current exceeds the pre-programmed threshold current value, capable of measuring probe impedance between the connector head terminals, comparing the impedance value thus measured with a pre-programmed impedance threshold, and delivering a signal of potential initial connection in the event of measured impedance lower than said impedance threshold.

6. The device of claim 5, wherein the scanning means further comprise controlling means triggered in response to delivery of the signal of potential initial connection, and capable of:
   initiating a temporization for a second time interval;
   at the end of said temporization, reiterating activation of the impedance test means; and
   in the event of test delivering a signal of potential initial connection again, delivering a signal of confirmation of initial connection.

7. The device of claim 6, wherein the scanning means further comprise means, triggered in response to the delivery of a signal confirming initial connection, capable of operating the generator from a mode of simultaneous monopolar and bipolar stimulation, to a mode of monopolar stimulation only.

8. The device of claim 6, wherein the scanning means further comprise means, triggered in response to delivery of a signal confirming initial connection, capable of detecting the type of probe, monopolar or bipolar, whose electrodes are connected to said at least two terminals.

9. The device of claim 8, wherein the means capable of detecting the type of probe, monopolar or bipolar, further comprise means for measuring probe impedance between at least two terminals of the connector head, and means capable of comparing the value of the measured impedance with a pre-programmed threshold of probe discrimination.

10. The device of claim 8, further comprising means capable of configuring, in response to the type of probe detected, the operating mode, monopolar or bipolar, of the circuits of stimulation and detection of the generator associated with the probe.

11. An active implantable medical device comprising:
   a case, said case comprising a generator and a power supply battery connected to the generator, said battery having an output current, and said generator producing stimulation impulses from said output current including monopolar stimulation impulses and bipolar stimulation impulses;
   a connector head connected to said case and equipped with at least two terminals capable of being connected to electrodes of a detection and stimulation probe, said probe capable of being a monopolar probe or a bipolar probe; and
   a circuit for detecting the initial connection of a probe to the connector, said circuit comprising:
      a battery consumption scanning circuit connected between the battery and the generator and coupled to the battery output current and having a resistor and an output corresponding to a measured value of the current;
      a first comparator having as a first input the measured value of the current over a first time interval and as a second input a pre-programmed threshold current value, and an output corresponding to a probe connected to said connector head terminals when said measured value of the current exceeds said pre-programmed threshold current value; and
      a detector circuit responsive to the measured value of the current not exceeding the pre-programmed threshold current value coupled to said at least two terminals and having an output signal responsive to a spontaneous depolarization detected at said terminals;
      a counter responsive to said detector circuit output signals for accumulating a count of detected depolarizations; and
      a second comparator having as a first input the accumulated count of detected spontaneous depolarizations and as a second input a pre-programmed counting threshold, and an output corresponding to a signal of potential initial connection in response to the accumulated count crossing the counting threshold to change a functional mode of the device.

12. The device of claim 11, wherein the battery consumption scanning circuit further comprises an integrator circuit capable of delivering with regular intervals a succession of measured values representative of the value of the battery output current, integrated throughout a predetermined integration period.

13. The device of claim 11, wherein the battery consumption scanning circuit further comprises an analog to digital converter having as an analog input the measured value of the current and a digital output corresponding to said measured value.

14. The device of claim 13, wherein the battery consumption scanning circuit further comprises a summing circuit having a predetermined summation period and an output corresponding to a cumulative sum of the measured value of the current during said summation period.

15. The device of claim 11, further comprising:
   an impedance test circuit coupled to the connector head terminals and having an output corresponding to an impedance measured between said terminals conditionally activated in the event the measured value of the current crosses the threshold current value, capable of measuring probe impedance between said terminals; and
   a comparator having as a first input said output corresponding to the measured impedance value and a second input a pre-programmed impedance threshold, and an output corresponding to a signal of potential initial connection in response to the measured impedance being lower than said impedance threshold.

16. The device of claim 15, wherein the battery consumption scanning circuit further comprises a control circuit, triggered in response to delivery of the signal of potential initial connection, operable to:
   initiate a temporization for a second time interval;
   at the end of said temporization, reiterate activation of the impedance test circuit; and
   in the event of said impedance test circuit output being a signal of potential initial connection again, delivering an output corresponding to a confirmation of initial connection.

17. The device of claim 16, wherein the battery consumption scanning circuit further comprises a control circuit coupled to said generator having an output control signal, triggered in response to the delivery of a signal confirming initial connection, to operate the generator in a mode of monopolar stimulation only.

18. The device of claim 16, wherein the battery consumption scanning circuit further comprises a probe detector circuit coupled to said connector head terminals, triggered in response to delivery of a signal confirming initial connection, able to detect whether a monopolar or bipolar probe is connected to said at least two terminals.

19. The device of claim 18, wherein the probe detector circuit further comprises an impedance measuring circuit coupled to said detector for measuring probe impedance between said at least two terminals of the connector head and having an output corresponding to a probe impedance between said at least two terminals, and a comparator having as a first input a value of the measured impedance, as a second input a pre-programmed threshold of probe discrimination, and an output corresponding to a monopolar probe when said first input is greater than said probe discrimination threshold and a bipolar probe when said impedance is below said probe discrimination threshold.

20. The device of claim 18, further comprising a control circuit capable of configuring, in response to whether a monopolar or bipolar probe is detected, the operating mode of the circuits of stimulation and detection of the generator associated with said detected probe.

* * * * *